US00PP29508P2

(12) United States Plant Patent
Ichie

(10) Patent No.: US PP29,508 P2
(45) Date of Patent: Jul. 17, 2018

(54) ***HYDRANGEA* PLANT NAMED 'ICH10162B'**

(50) Latin Name: *Hydrangea macrophylla*
Varietal Denomination: ICH10162B

(71) Applicant: Toyokazu Ichie, Kakegawa (JP)

(72) Inventor: Toyokazu Ichie, Kakegawa (JP)

( * ) Notice: Subject to any disclaimer, the term of this patent is extended or adjusted under 35 U.S.C. 154(b) by 0 days.

(21) Appl. No.: 15/731,147

(22) Filed: Apr. 26, 2017

(51) Int. Cl.
*A01H 5/00* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Audrey Charles

(57) ABSTRACT

A new and distinct cultivar of *Hydrangea* plant named 'ICH10162B', characterized by its double-type, light purple-pink colored inflorescences that are deep violet-blue colored when grown under acidic soil conditions, dark green-colored foliage, and moderately vigorous, upright growth habit, is disclosed.

1 Drawing Sheet

Latin name of genus and species of plant claimed: *Hydrangea macrophylla.*
Variety denomination: 'ICH10162B'.

BACKGROUND OF THE INVENTION

The present invention relates to a new and distinct cultivar of *Hydrangea* plant botanically known as *Hydrangea macrophylla* and hereinafter referred to by the cultivar name 'ICH10162B'.

The new cultivar originated in a controlled breeding program in Kakegawa, Japan during June 2010. The objective of the breeding program was the development of *Hydrangea* cultivars that have double-type inflorescences with attractive coloration.

The new *Hydrangea* cultivar is the result of cross-pollination. The female (seed) parent of the new cultivar is Ohayo, not patented, characterized by its double-type, purple-pink colored inflorescences (violet-blue colored when grown under acidic soil conditions), dark green-colored foliage, and vigorous, upright growth habit. The male (pollen) parent of the new cultivar is a proprietary *Hydrangea macrophylla* breeding selection coded 08-23A, not patented, characterized by its single-type, deep purple-pink colored inflorescences (deep violet-blue when grown under acidic soil conditions) with the sterile florets having a white margin, dark green-colored foliage, and moderately vigorous, upright growth habit. The new cultivar was discovered and selected as a single flowering plant within the progeny of the above stated cross-pollination during June 2012 in a controlled environment in in Kakegawa, Japan.

Asexual reproduction of the new cultivar by terminal stem cuttings since June 2012 in Kakegawa, Japan and West Grove, Pa. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'ICH10162B' as a new and distinct cultivar of *Hydrangea* plant:

1. Double-type, light purple-pink colored inflorescences that are deep violet-blue colored when grown under acidic soil conditions;
2. Dark green-colored foliage; and
3. Moderately vigorous, upright growth habit.

Plants of the new cultivar differ from plants of the female parent primarily in having deeper colored inflorescences when grown under acidic soil conditions and less growth vigor. Plants of the new cultivar differ from plants of the male parent primarily in flower type and sterile floret margin color.

Of the many commercially available *Hydrangea* cultivars, the most similar in comparison to the new cultivar is Ruby Blossom 'B-003', U.S. Plant Pat. No. 26,823. However, in comparison, plants of the new cultivar differ from plants of 'B-003' in at least the following characteristics:

1. Plants of the new cultivar have more sterile florets per inflorescence than plants of 'B-003';
2. Plants of the new cultivar have a sepal margin different from plants of 'B-003'; and
3. Plants of the new cultivar have darker colored foliage than plants of 'B-003'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'ICH10162B'. The plants were approximately 11 month old and grown in 3-gallon containers in an outdoor nursery in West Grove, Pa. for approximately 8 months then transferred for flowering to greenhouse conditions for approximately 3 months.

DETAILED BOTANICAL DESCRIPTION

Figure 1:
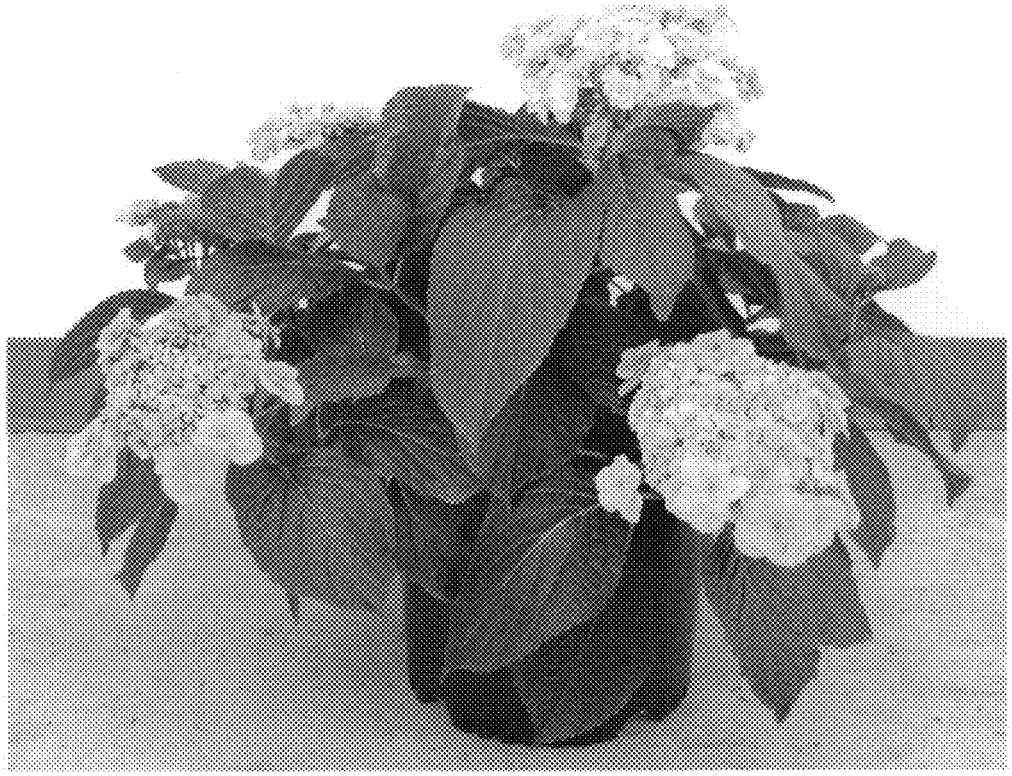
FIG. 1 illustrates a side view of the overall growth and flowering habit of 'ICH10162B'.
Figure 2:
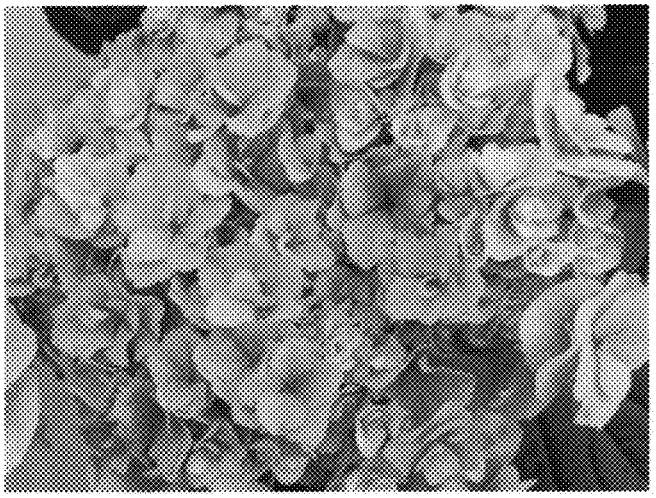
FIG. 2 illustrates a close-up view of an individual inflorescence of 'ICH10162B'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in March 2017 under natural light conditions in West Grove, Pa.

The following descriptions and measurements describe approximately 11 month old plants produced from cuttings from stock plants. The plants were grown in 3-gallon containers utilizing a soilless growth medium in an outdoor nursery in West Grove, Pa. for approximately 8 months. To flower, plants were moved to greenhouse conditions for approximately 3 months. Greenhouse temperatures were maintained at 74° F. to 80° F. (23° C. to 27° C.) during the day and approximately 66° F. to 70° F. (19° C. to 21° C.) during the night. Greenhouse light levels of 5,010 footcandles to 8,016 footcandles were maintained during the day. Measurements and numerical values represent averages of typical plants.

Botanical classification: *Hydrangea macrophylla* 'ICH10162B'.

Parentage:

*Female parent*.—Ohayo, not patented.

*Male parent*.—Proprietary *Hydrangea macrophylla* breeding selection coded 08-23A, not patented.

Propagation:

*Type cutting*.—Softwood cuttings.

*Time to initiate roots during the summer*.—Approximately 16 days.

*Time to produce a rooted cutting during the summer*.—Approximately 28 days.

*Root description*.—White to grey, medium thickness, fibrous.

*Rooting habit*.—Moderate branching and density.

Plant description:

*Commercial crop time*.—Approximately 12 months from a rooted cutting to finish in a 3 gallon pot.

*Growth habit and general appearance*.—Deciduous shrub, mophead-type *Hydrangea*; moderately vigorous, upright growth habit.

*Hardiness*.—USDA Zone 6b (−5° F. to 0° F.).

*Heat tolerance*.—Regularly tolerates temperatures as high as 93° F. (33.9° C.) in the summer.

*Size*.—Height from soil level to top of plant plane: Approximately 40.0 cm. Width: Approximately 65.0 cm.

*Branching habit*.—Freely branching. Pinching enhances branching. Quantity of lateral branches per plant: Approximately 8 to 10.

*Branch*.—Shape: Rounded. Strength: Strong. Length to base of inflorescence: Approximately 33.0 cm. Diameter: Approximately 6.0 mm. Length of central internode: Approximately 5.5 cm. Texture of young stem: Glabrous. Texture of mature stem: Woody. Color of young stem: Between 144A and 144B. Color of mature stem: Closest to N199A.

*Lenticels*.—Quantity per internode: Approximately 70 to 80. Shape: Round to elliptic. Size: Approximately 1.0 mm to 2.0 mm. Color: Closest to N92A.

Foliage description:

*General description*.—Quantity of leaves per lateral branch: Approximately 12. Fragrance: None detected. Form: Simple. Arrangement: Opposite.

*Leaves*.—Aspect: Flat. Shape: Elliptic. Margin: Serrated. Apex: Acuminate. Base: Rounded. Venation pattern: Pinnate. Length of mature leaf: Approximately 17.0 cm. Width of mature leaf: Approximately 12.5 cm. Texture of upper and lower surfaces: Coriaceous, glabrous. Color of upper surface of young foliage: 137A with venation of 137C. Color of lower surface of young foliage: 137B with venation of 137C. Color of upper surface of mature foliage: Between 139A and 136A with venation of 139B. Color of lower surface of mature foliage: 138A with venation of 138B.

*Petiole*.—Length: Approximately 2.0 cm. Diameter: Approximately 5.0 mm. Texture: Glabrous. Color: 144A.

Flowering description:

*Flowering habit*.—Seasonal, May through August.

*Lastingness of individual inflorescence on the plant*.—Persistent, with color retained for about 3 to 4 weeks.

Inflorescence description:

*General description*.—Type: Terminal globular, mophead, compound corymb of double, rotate-shaped, sterile flowers composed of an average of 12 to 18 sepals, fertile flowers form buds that do not open. Quantity per plant: Approximately 6. Fragrance: None detected. Aspect: Face upward and outward. Height: Approximately 7.0 cm. Width: Approximately 18.0 cm. Quantity of fertile florets per inflorescence: Approximately 300. Quantity of sterile florets per inflorescence: Approximately 150.

*Peduncle*.—Strength: Strong. Shape: Rounded. Length: Approximately 3.0 cm. Diameter: Approximately 5.0 mm. Texture: Glabrous. Color: 144A with hints of 186B.

Floret description:

*General description*.—Type: Double, sterile and fertile; fertile flowers form buds that do not open.

*Sterile florets, bud just before opening*.—Shape: Globular. Length: Approximately 5.0 mm. Diameter: Approximately 5.0 mm. Color: 145A.

*Sterile florets*.—Depth: Approximately 1.5 cm. Diameter: Approximately 2.5 cm to 4.5 cm. Corolla: Does not fully form, indistinguishable.

*Sepals, sterile florets*.—Shape: Broadly obovate. Margin: Entire, crenate along mid-section. Apex: Rounded. Base: Attenuate. Length: Approximately 1.3 cm to 2.0 cm. Width: Approximately 1.1 cm to 2.5 cm. Texture of upper and lower surfaces: Glabrous. Color of upper surface when first open: 68B transitions to 62B and finally 62D at the base; inner sepals are 62D to 158B. Color of lower surface when first open: 65B transitioning to 65D and 155B at the base. Color of upper surface when fully open: 68B. Color of lower surface when fully open: 73B.

*Pedicel, sterile florets*.—Strength: Strong. Aspect: Erect. Length: Approximately 1.0 to 2.0 cm. Diameter: Approximately 2.0 mm. Texture: Sparsely pubescent with appressed hairs. Color: NN74C.

*Fertile florets, bud*.—Shape: Globular. Length: Approximately 1.0 mm. Diameter: Approximately 1.0 mm. Color: 145A.

*Reproductive organs*.—Not observed.

Seed and fruit production: Neither seed nor fruit production has been observed.

Disease and pest resistance: Resistance to pathogens and pests common to *Hydrangea* has not been observed.

What is claimed is:

1. A new and distinct cultivar of *Hydrangea* plant named 'ICH10162B', substantially as herein illustrated and described.

* * * * *